United States Patent
Heni et al.

(10) Patent No.: US 10,122,897 B2
(45) Date of Patent: Nov. 6, 2018

(54) DEVICE FOR RECORDING AN IMAGE OF AN OBJECT FIELD ON A HUMAN OR ANIMAL BODY

(71) Applicant: Karl Storz SE & Co. KG, Tuttlingen (DE)

(72) Inventors: Andreas Heni, Fridingen (DE); Markus Kupferschmid, Emmingen-Liptingen (DE); Daniel Ulmschneider, Nendingen (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 200 days.

(21) Appl. No.: 14/494,785

(22) Filed: Sep. 24, 2014

(65) Prior Publication Data

US 2015/0085084 A1    Mar. 26, 2015

(30) Foreign Application Priority Data

Sep. 24, 2013   (DE) .................. 10 2013 110 543

(51) Int. Cl.
| | |
|---|---|
| H04N 5/225 | (2006.01) |
| A61B 1/00 | (2006.01) |
| H04N 13/211 | (2018.01) |
| G02B 23/24 | (2006.01) |

(Continued)

(52) U.S. Cl.
CPC ....... *H04N 5/2252* (2013.01); *A61B 1/00064* (2013.01); *A61B 1/00096* (2013.01); *A61B 1/00147* (2013.01); *A61B 1/00177* (2013.01); *A61B 1/00193* (2013.01);

(Continued)

(58) Field of Classification Search
None
See application file for complete search history.

(56) References Cited

U.S. PATENT DOCUMENTS

| | | | | |
|---|---|---|---|---|
| 5,166,787 A | * | 11/1992 | Irion .................. | A61B 1/00181 348/75 |
| 5,538,497 A | * | 7/1996 | Hori .................. | A61B 1/00096 385/117 |
| 5,689,365 A | | 11/1997 | Takahashi | |

(Continued)

FOREIGN PATENT DOCUMENTS

| | | |
|---|---|---|
| DE | 102011001200 A1 | 9/2011 |
| DE | 102011054031 A1 | 10/2012 |

(Continued)

OTHER PUBLICATIONS

European Search Report Application No. EP18166579 Completed: Jul. 18, 2018; dated Jul. 31, 2018 10 pages.

*Primary Examiner* — Mohammad J Rahman
(74) *Attorney, Agent, or Firm* — Whitmyer IP Group LLC

(57) ABSTRACT

A device for recording an image of an object field on a human or animal body from outside of the body including a shaft and an observation optical system, arranged at a distal end of the shaft, for recording the image of the object field, wherein the observation optical system is embodied as a stereo optical system including an electronic image recorder for recording a stereo image of the object field and wherein the device includes an optical unit, which includes the observation optical system and is rotatable about a first axis of rotation approximately parallel to a direction of view of the observation optical system.

12 Claims, 4 Drawing Sheets

(51) Int. Cl.
*A61B 90/30* (2016.01)
*A61B 90/00* (2016.01)

(52) U.S. Cl.
CPC ....... *G02B 23/2415* (2013.01); *H04N 13/211* (2018.05); *A61B 2090/306* (2016.02); *A61B 2090/3616* (2016.02)

(56) References Cited

U.S. PATENT DOCUMENTS

| | | | | |
|---|---|---|---|---|
| 6,425,857 | B1* | 7/2002 | Rudischhauser | A61B 1/00195 600/112 |
| 6,666,854 | B1* | 12/2003 | Lange | A61B 17/2909 606/1 |
| 9,176,580 | B2* | 11/2015 | Moraviec | G06F 3/012 |
| 2001/0055462 | A1* | 12/2001 | Seibel | A61B 1/00048 385/147 |
| 2003/0092966 | A1* | 5/2003 | Schara | A61B 1/00183 600/173 |
| 2004/0246469 | A1* | 12/2004 | Hirose | A61B 1/00048 356/139.03 |
| 2005/0026104 | A1 | 2/2005 | Takahashi | |
| 2005/0119529 | A1* | 6/2005 | Farr | G02B 25/001 600/160 |
| 2008/0051628 | A1* | 2/2008 | Pecherer | A61B 1/267 600/112 |
| 2008/0300457 | A1* | 12/2008 | Hosaka | A61B 1/00096 600/110 |
| 2010/0081875 | A1* | 4/2010 | Fowler | A61B 1/00149 600/114 |
| 2010/0245549 | A1 | 9/2010 | Allen et al. | |
| 2011/0058716 | A1 | 3/2011 | Okawa et al. | |
| 2011/0230713 | A1* | 9/2011 | Kleemann | A61B 1/00165 600/106 |
| 2011/0230894 | A1* | 9/2011 | Simaan | A61B 1/00183 606/130 |
| 2011/0235324 | A1 | 9/2011 | Irion et al. | |
| 2012/0265023 | A1* | 10/2012 | Berci | A61B 90/30 600/249 |
| 2013/0102846 | A1* | 4/2013 | Sjostrom | A61B 1/07 600/110 |
| 2013/0162776 | A1* | 6/2013 | Noack | A61B 1/0008 348/45 |
| 2014/0081169 | A1* | 3/2014 | Gerding | A61B 1/015 600/560 |
| 2014/0303439 | A1* | 10/2014 | Scherr | A61B 1/00096 600/112 |
| 2016/0286197 | A1* | 9/2016 | Schwarz | A61B 1/00096 |

FOREIGN PATENT DOCUMENTS

| | | |
|---|---|---|
| DE | 102011090132 A1 | 7/2013 |
| EP | 1759629 A1 | 3/2007 |
| JP | H10192233 A | 7/1998 |
| WO | 9413190 A1 | 6/1994 |
| WO | 0230348 A2 | 4/2002 |
| WO | 2012075155 A2 | 6/2012 |

\* cited by examiner

DEVICE FOR RECORDING AN IMAGE OF AN OBJECT FIELD ON A HUMAN OR ANIMAL BODY

FIELD OF THE INVENTION

The present invention relates to a device for recording an image of an object field on a human or animal body.

BACKGROUND OF THE INVENTION

DE 10 2011 054 031 A1 has disclosed a device for observing and illuminating an object field on a patient from a location away from the body of the patient, comprising an optical system for observing the object field and an illumination apparatus for illuminating the object field. The device furthermore comprises a shaft, at the distal end of which a head part is arranged, which head part is widened compared to the shaft and in which at least one emitting illumination unit for homogeneous illumination of the object field is arranged. Feed lines for the at least one illumination unit extend through the shaft. Furthermore, the elongate shaft can hold an image forwarding apparatus, which forwards the image of the operation field to a proximal end of the shaft. Such a device is also referred to as "exoscope". Exoscopes of the aforementioned type, going by the name of VITOM®, are offered by KARL STORZ GmbH & Co. KG.

In particular, such an exoscope enables the illumination and observation of an operation field during a surgical operation from a working distance of e.g. 20 to 75 cm such that the work space of the surgeon remains practically unrestricted by the exoscope. The relatively thin shaft holds the lines to the head part such that there is no need for exposed lines, which could hinder the surgeon. Connecting a video camera allows the image of the object field to be depicted on a screen, and so the latter can be observed by the surgeon without tiring; furthermore, this renders it possible for the object field to be observed by more people and for the image to be recorded, for example for documentation purposes.

The exoscope can be held by a holder having a hinged arm, at the distal end of which a gripper embodied for securely holding the exoscope, for example for gripping and damping the shaft, is arranged. By adjusting the holder it is possible to secure the exoscope at a suitable distance from the object field and in a suitable position and with suitable alignment, depending on the requirements, if the optical system of the exoscope is embodied as a side-viewing optical system with a direction of view that makes an angle of approximately 90° with the longitudinal axis of the shaft, the exoscope can be positioned, in particular, over the object field with a perpendicularly downwardly directed direction of view for observing a horizontally arranged object field, which may, for instance, be an operation field in the case of a surgical operation on the human body. By adjusting the holder, the exoscope can be brought into different positions while keeping approximately the same direction of view and, for this purpose, be swiveled about a vertical axis, depending on requirements and depending on the side from which unhindered access to the operation field is required.

In the known exoscope, the optical system is embodied as a monocular optical system, as a result of which only a restricted spatial perception of the object field is possible. However, a spatial perception of the object field may help the surgeon when performing a surgical operation. What is known from other fields of application, such as endoscopy, is that an improved spatial perception of the object field is possible using a stereoscopic optical system, in which two images of the object field are recorded from slightly different perspectives. The two images which, together, make up the stereoscopic image are also referred to as "half images". Two observation strands are required for recording the two half images, said observation strands, in particular, respectively comprise an objective, wherein the stereo basis is determined by the distance between the two objectives perpendicular to the direction of view. The two half images are displayed to an observer in such a way that the observer obtains a spatial impression of the object field. To this end, a screen, for example, with a changing polarization may be provided in a manner known per se, with the observer wearing polarization spectacles with different polarizations of the two lenses.

However, the problem arising here in the case of a generic device for recording an image of an object field on a human or animal body is that the image generated on an electronic image recorder, and therefore also the image of the operation field displayed on a screen, rotates when the shaft rotates about an axis approximately parallel to the direction of view of the optical system. When use is made of a stereo optical system, the baseline of the stereoscopic optical system additionally rotates; therefore, the stereo basis is no longer displayed horizontally on the screen, and so the stereo effect, and hence also the spatial impression, may be lost. As a result, the orientation in the operation field is made more difficult, or even impossible, for a surgeon observing the screen.

JP 10192233 A has disclosed a stereoscopic electronic endoscope comprising an oblique view optical system, wherein provision is made for a motor-driven adjustment of a rotation element, which supports an optical system comprising two objective lens systems which are spaced apart transversely in relation to the optical axis, and two CCD image recorders assigned thereto. U.S. Pat. No. 5,689,365 has disclosed a stereoscopic endoscope, which comprises a front optical system with a single optical axis and a rear optical system with a plurality of optical axes. Together with two photoelectric image recorders, the rear optical system can be rotated about an axis parallel to the shaft of the endoscope relative to the front optical system.

SUMMARY OF THE INVENTION

It is an object of the present invention to specify a generic device which enables the spatial depiction and perception of the object field, wherein the aforementioned disadvantages can be avoided.

This object is achieved by a device in accordance with the invention.

A device according to the invention for recording an image of an object field on a human or animal body from a position outside of the human or animal body comprises a shaft, which preferably has an elongate and rigid embodiment, and an observation optical system, arranged at a distal end of the shaft, for recording the image of the object field. Alternatively, the shaft can also have a very short embodiment. The object field is arranged on the surface of the human or animal body or is at least partly observable from outside of the body; in particular, the object field is an operation field of a surgical operation. In this case, outside means that the device is situated completely outside of the body at all times. The device preferably has a distance of at least 15 cm from the body. An apparatus for forwarding the recorded image to a proximal end region of the shaft is held within the shaft, wherein connectors may be provided for connecting feed, evaluation and/or display apparatuses. In particular, a feed and/or signal cable of an electronic image recorder assigned to the observation optical system may be guided in the shaft from the distal end to the proximal end region of the shaft. Furthermore, e.g. optical waveguides may be arranged in the shaft in order to forward illumination light to the distal end of the shaft, where an illumination apparatus for illuminating the object field may be provided. Preferably, the illumination apparatus is arranged proximally from the observation optical system in the distal end region of the device.

According to the invention, the observation optical system is embodied as a stereo optical system comprising at least one electronic image recorder for recording a stereo image of the object field. By way of example, the at least one electronic image recorder may be a CCD (charge-coupled device). In particular, such a stereo optical system comprises a plurality of objectives, which are spaced apart in a direction across a direction of view of the observation optical system and which each generate an image of the object field on respectively one, or else on a common, assigned electronic image recorder. The objectives and image recorder are arranged within the optical unit, in particular, the objectives are arranged with a fixed spatial relationship to one another, wherein the distance between two objectives measured across the direction of view represents the stereo basis. With the respective optical axes thereof, the objectives are arranged parallel or at an angle with respect to one another, which angle is determined by the stereo basis and the desired working distance. What is possible to achieve by an angled arrangement is that the center of each half image of the stereoscopic image represents the same point of the object field at the preferred working distance. In the case where the optical axes of the objectives are at an angle with respect to one another, the "direction of view" of the observation optical system denotes a mean direction between the optical axes.

According to the invention, the observation optical system embodied as a stereo optical system is comprised by an optical unit, which is rotatable about a first axis of rotation approximately parallel to the direction of view. The optical unit is arranged at the distal end of the shaft, for example in a distal end section of the shaft or in a head part of the device, arranged at the distal end section of the shaft. The first axis of rotation is preferably directed parallel to the direction of view of the observation optical system or only angled in relation to the direction of view by at most such an angle that the point at which the first axis of rotation intersects the object field is contained in the stereoscopic half images, independently of the rotation of the optical unit about the first axis of rotation. The stereo optical unit itself can form the rotatable optical unit. Preferably, the optical unit is embodied as a compact unit, in which the stereo optical system is held, and comprises, in particular, a cylindrical lateral surface. The optical unit may comprise further mechanical, optical and/or electronic components.

What is enabled by virtue of the device comprising an optical unit rotatable about a first axis of rotation approximately parallel to the direction of view and said optical unit comprising an observation optical system embodied as a stereo optical system is the recording of a stereoscopic image of the object field and, when the device according to the invention is swiveled, both an erecting of the recorded and depicted image of the object field and an adjusting of the stereo basis. What this renders possible is that the recorded stereoscopic image can be depicted with a substantially unmodified alignment and in such a way that the user or observer can perceive the stereo effect, even after swiveling the device. This can thereby avoid the spatial impression being lost and the orientation being made more difficult as a result of the rotation of the depicted images and the stereo basis on a screen.

Preferably, the optical unit comprises at least two electronic image recorders, of which each one is assigned an objective for recording a half image of the stereoscopic image of the object field. In a particularly preferred manner, the optical unit comprises exactly two objectives and two electronic image recorders, which respectively record a half image of the stereoscopic image. Within the optical unit, the two objectives and the respectively assigned image recorders thereof are fixedly arranged, wherein the distance measured across the direction of view represents the stereo basis and the angle bisector between the optical axes of the objectives in the direction of view. A particularly simple arrangement for recording a stereoscopic image is enabled as a result of the optical unit comprising two objectives, fixedly arranged in the optical unit, with respectively one electronic image recorder.

The optical unit may furthermore comprise further image recorders for recording images, in particular in specific wavelength ranges. By way of example, image sensors or optical components for fluorescence diagnostics may be provided. The image sensors may be embodied to detect light in non-visible wavelength ranges.

In accordance with a preferred embodiment of the invention, the device comprises a hermetically sealed housing, within which the optical unit is held and mounted in a rotatable manner, in particular, the housing has such a hermetically sealed embodiment that no ingress of vapor into the housing is possible or at least this cannot occur to any meaningful extent, even under the temperature and pressure conditions occurring during the sterilization in an autoclave. The housing therefore forms a sleeve by means of which the optical unit is hermetically separated from the surroundings. The housing preferably has a metallic embodiment, in particular made of a non-ferromagnetic metal; by way of example, aluminum and austenitic steels are suitable for this. The housing comprises at least one transparent window inserted in a hermetically sealed manner, through which the stereo optical system records the respective half images which image the object field. The housing, which is preferably stationary relative to the device, can for example be embodied as a housing of a head part arranged at the distal end of the shaft, which head part is widened in relation to the shaft, but it may also constitute a distal end section of the shaft itself. The housing can be restricted to a distal end region of the device or extend into the shaft or form a hermetically sealed sleeve together with the shaft. It may also surround the whole device so that all components in the housing are arranged in a manner hermetically sealed off from the outside. It is rendered possible to embody the device as an autoclavable instrument as a result of the device comprising a hermetically sealed housing, within which the optical unit is held in a rotatable manner. As a result of this, the hygienic requirements for use in the sterile region of an operating theater can be satisfied in a simple manner, without the service life of the optical and electronic components contained in the optical unit being substantially restricted.

Preferably, an illumination apparatus comprises a window at the distal end of the device, which window is connected to the housing in a hermetically sealed manner.

In order to rotate the optical unit for erecting the recorded image and for setting the stereo basis, provision can be made within the hermetically sealed housing for an electric motor drive, which can be actuated from outside of the housing. This may enable an automatic alignment, particularly in the case where a swivel movement of the device is detected by one or more sensors. By way of example, such a swivel movement can be detected by gravitational sensors, inertial sensors or sensors of a positioning system.

In accordance with a preferred embodiment of the invention, a magnetic drive is provided for bringing about the rotation of the optical unit, which magnetic drive comprises at least one first magnetic coupling element arranged outside of the housing, said magnetic coupling element interacting with at least one second magnetic coupling element arranged within the housing. The second magnetic coupling element is assigned to the optical unit in order to rotate the optical unit about the first axis of rotation. Permanent magnets, in particular, can be provided as magnetic coupling elements, wherein the first and the second magnetic coupling elements can be arranged with opposing equal or opposite poles in order to bring about magnetic coupling by magnetic attractive or repulsive forces. Non-magnetized ferromagnetic elements, which interact with permanent magnetic coupling elements as a result of the generated attractive forces, may also serve as magnetic coupling elements. The first magnetic coupling element or elements may be arranged on a first magnet support, which can be actuated from the outside, and the second magnetic coupling element or elements may be arranged on a second magnet support, which is connected to the optical unit for rotation therewith. Arranged between the first and the second coupling elements is at least one wall of the housing, through which the magnetic coupling acts, and which, to this end, is made with a sufficiently thin wall and/or from a non-ferromagnetic material. The magnetic drive is actuatable in a manual or motor-driven manner from outside of the housing in order to rotate the optical unit about the first axis of rotation, in this manner, a rotation of the optical unit is made possible by an actuation from outside of the hermetically sealed housing. As a result of this, it is possible to develop an autoclavable exoscope, in which erecting the recorded image and aligning the stereo basis are possible in a particularly simple manner.

It is furthermore preferable for the magnetic drive to be connected to an operating element, for example a rotary knob, for rotation therewith, which operating element is rotatable about a second axis of rotation which is substantially parallel to, and preferably coincides with, the first axis of rotation. This enables a manual adjustment of the optical unit in a simple and intuitive manner. Therefore, after swiveling of the exoscope, a user can both erect the reproduced image and reestablish the stereo effect by a simple rotation of the operating element. Byway of example, the operating element can be embodied as a rotary lever or as a rotary knob and may comprise grip depressions or grip grooves in order to simplify the operation. In particular, the first magnet support, which supports the first magnetic coupling elements, may be connected to the rotary knob for rotation therewith or it may be embodied as such a rotary knob itself, as a result of which a particularly simple embodiment of the device is made possible.

In accordance with a particularly preferred embodiment of the invention, the device is embodied with a direction of view of the observation optical system angled relative to a longitudinal axis of the shaft.

In particular, the direction of view is aligned at approximately 90° in relation to the longitudinal axis of the shaft.

For an exoscope, an angled direction of view, in particular perpendicular to the shaft, is particularly advantageous since it allows the device to be used to observe and illuminate a location without the device being in the way of an operator in the process. Particularly if the person looks at the same location and, in the process, is situated behind the instrument, it is advantageous if said instrument, with all the proximal connectors thereof, leads away laterally from the observed location and from the person. Preferably, a present illumination unit is also aligned in the direction of view.

In a particularly preferred embodiment of the invention, the operating element is embodied as a rotary cap, which is placed onto a head part of the shaft containing the rotatable optical unit on a side opposing the direction of view. The head part is widened, in particular in relation to the shaft, on the distal end of which it is arranged. The head part itself may be embodied as a hermetically sealed housing or as part of such a housing or it may comprise at least part of a hermetically sealed housing, wherein the optical unit is mounted in a rotatable manner within the hermetically sealed housing. As a result of the operating element being embodied as a rotary cap placed on a side of the head part, a simple assembly of the device and a simple and intuitive adjustment of the optical unit is made possible.

Preferably, the at least one second magnetic coupling element is arranged on an outer lateral surface of the second magnet support, which has a substantially cylindrical embodiment and which is held with the optical unit for rotation therewith in the hermetically sealed housing. In particular, a plurality of second magnetic coupling elements are present, which can be distributed uniformly in the circumferential direction on the outer lateral surface of the second magnet support. Accordingly, the at least one first magnetic coupling element is arranged on an inner side of a first magnet support which is connected to the operating element for rotation therewith, which first magnet support is embodied as a cylindrical rotary ring and arranged outside of the housing. The first magnet support surrounds the second magnet support on the outer side thereof with a small distance therefrom, wherein a wall of the housing is arranged between the first and the second magnet support. The first magnet support preferably comprises a plurality of first magnetic coupling elements, which may be distributed uniformly in the circumferential direction on the inner side of the first magnet support and which are arranged in such a way that they interact with a plurality of second magnetic coupling elements in order to transmit a torque from the first to the second magnet support. As a result of the fact that the second magnetic coupling element or elements assigned to the optical unit is/are arranged on the outer lateral surface of the second magnet support and the first magnetic coupling element or elements assigned to the operating element is/are arranged on the inner surface of the first magnet support, with the first magnet support surrounding the second magnet support, a magnetic coupling with a particularly large diameter, and therefore the transmission of a particularly large torque and a particularly fine adjustment of the optical unit, is made possible.

In accordance with a further preferred embodiment, the first magnet support, which supports the at least one first magnetic coupling element connected to the operating element, has a substantially cylindrical embodiment, wherein the at least one first magnetic coupling element is arranged on a lateral surface of the first magnet support. Accordingly, the second magnet support, which supports the at least one second magnetic coupling element connected to the optical unit, has a substantially ring-shaped embodiment, wherein the at least one second magnetic coupling element is arranged on an inner side of the second magnet support. The first magnet support engages with the second magnet support, wherein a small spacing, in which a wall of the housing is arranged, remains between the first and the second magnet support. Therefore, the housing has a cup-shaped embodiment in this region and surrounds the ring-shaped second magnet support on the inner and outer side, wherein the first magnet support engages with the depression formed by the cup-shaped embodiment. This enables a particularly secure connection between the first magnet support and the housing, particularly in the case where a rotary knob is arranged outside of the second magnet support, said rotary knob overlapping said second magnet support and a further wall of the housing.

Advantageously, provision can also be made for first magnetic coupling elements to be arranged both on an inner side of a rotary ring connected to the operating element for rotation therewith and on the outer side of a cylinder connected to the operating element for rotation therewith, wherein a gap is formed between the cylinder and the rotary ring. In this case, the second magnetic coupling elements are arranged both on an outer lateral surface of a cylindrical ring connected to the optical unit for rotation therewith, which cylindrical ring engages into the gap between the cylinder and the rotary ring, and on an inner side of the cylindrical ring, or they are held in the cylindrical ring in such a way that a magnetic coupling effect is rendered possible both in respect of the inner and the outer second magnetic coupling elements. The ring connected to the optical unit for rotation therewith is surrounded on the inner and outer side by walls of the housing. This enables a particularly effective coupling and a particularly fine adjustment of the optical unit.

Preferably, provision is made for both at least one stop for the rotational movement of the optical unit and for at least one stop for the rotation of the operating element, which stops serve to restrict the maximum angle of rotation possible in each case. In general, a maximum angle of rotation of ±90° is advantageous and sufficient. Furthermore, this allows a fixed angle relationship to be obtained between the operating element and the optical unit by adjustment against the stop of the operating element. In particular, this can undo an undesired skipping of individual coupling elements, for example by virtue of a torque furthermore being applied on the operating element after the optical unit has reached the stop thereof. As soon as both stops are reached, the original coupling between the operating element and the optical unit is reestablished. This simplifies the operation.

Furthermore, it is preferable for the operating element to have perceptible latching such that one or more preferred angle positions of the optical unit can easily be identified by a user. By way of example, a position in which a longitudinal central plane between the optical axes of the two objectives is perpendicular to the longitudinal axis of the shaft or a position in which the longitudinal axis of the shaft lies in the central plane between the two optical axes may be a preferred position of the optical unit. Furthermore, a perceptible or visible marking, for example a marking highlighted in color, may be provided on the operating element in order to identify a preferred angle position. This further simplifies the operation of the device.

Preferably, the optical unit is connected in a heat conducting manner to a heat conductor extending in the shaft. This enables the dissipation of the thermal losses arising during operation of the electronic image recorder or recorders such that it is possible to avoid heating up an outer surface of the exoscope to an inadmissible temperature, in particular to a temperature above approximately 48° C. By way of example, to this end, provision can be made for a heat pipe extending in the shaft to engage with the distal end thereof into a groove of a region of the housing adjacent to the optical unit, which surrounds the optical unit such that there is only a small gap between the optical unit and the region of the housing coupled to the heat pipe, or for said heat pipe to abut directly on an outer side of the optical unit. Alternatively or additionally, the optical unit may be mounted on heat-conducting slide bearings, for example made of bronze or a graphite film. Furthermore, alternatively or additionally, a wiper made of a metallic material or else made of graphite may abut against an outer surface of the optical unit in order to dissipate heat. The heat transmitted into the shaft in this manner can likewise be dissipatable to the proximal end of the shaft through a heat pipe, where it can be forwarded into the grip and emitted via the surface of the grip; however, a heat exchanger for further dissipation of the heat into an external cooling apparatus may also be arranged in the proximal end region of the shaft or in the grip. By means of such measures for dissipating heat, it also becomes possible to dissipate thermal losses introduced into the shaft and the distal end region thereof by the illumination apparatus.

It is understood that the features mentioned above and still to be explained below can be used not only in the respectively specified combination, but also in other combinations or on their own, without departing from the scope of the present invention.

BRIEF DESCRIPTION OF THE DRAWINGS

Further aspects of the invention emerge from the following description of a preferred exemplary embodiment and from the attached drawing, in detail.

DETAILED DESCRIPTION OF THE INVENTION

Figure 1A:
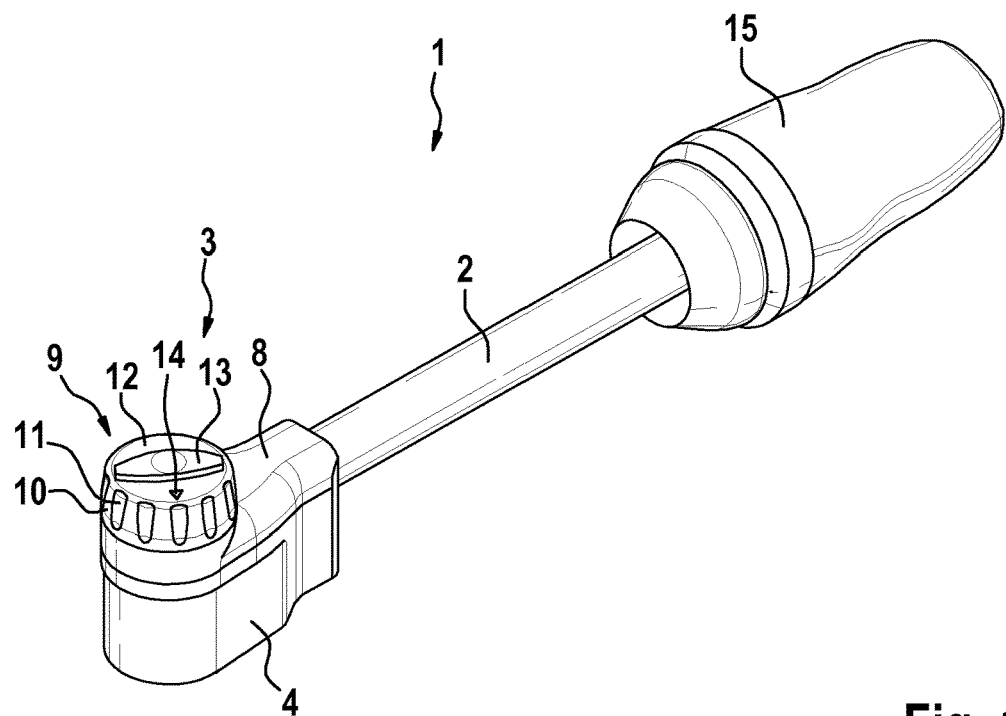
FIGS. 1a and 1b show an exemplary embodiment of a device according to the invention in two different perspective views.
Figure 1B:
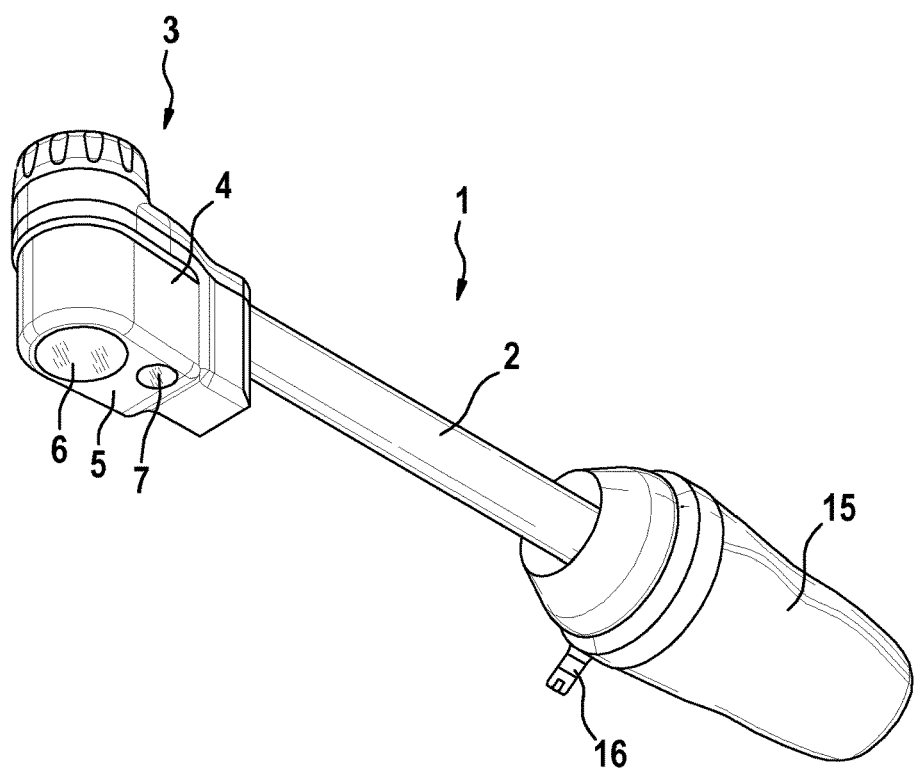

A device according to the invention, which is referred to as an exoscope 1 in the following text, is shown in two different perspective views in FIGS. 1a and 1b. The exoscope 1 comprises an elongate cylindrical shaft 2, at the distal end of which a head part 3, which is widened compared to the shaft, is arranged. The head part 3 comprises a housing 4, the distal region of which has an approximately semi-cylindrical form, wherein the axis of the semi cylinder is at an angle of approximately 90° with respect to the longitudinal axis of the shaft 2. An observation window 6, through which an observation optical unit arranged in the interior of the housing 4 receives light from an object field, is inserted into a base surface 5 of the housing. The base surface 5 furthermore comprises an illumination window 7, behind or in which an illumination optical system terminates and through which illumination light can be emitted for illuminating the object field. By way of example, the illumination optical system can be a light source arranged behind the illumination window 7 in the interior of the head part. However, optical waveguides may also terminate in the region of the illumination window 7 or the end surfaces of the optical waveguides themselves may form the illumination window 7, wherein the optical waveguides are guided through the shaft 2 and transmit light from a light source arranged outside of the head part 3. The observation window 6 is preferably a plane parallel plate, while the illumination window is preferably embodied as a convex lens.

A rotary cap 9 is placed on a distal end region of a cover surface 8 lying opposite the base surface 5, which rotary cap 9 comprises a plurality of grip depressions 11 on the circumferential side 10 thereof and supports a rotary grip 13 on the upper side 12 thereof. Furthermore, the rotary cap 9 comprises a marking 14, which makes it easy to identify the rotary position of the rotary cap 9. The exoscope 1 furthermore comprises a handle 15, which has a connector 16 for connecting signal and supply cables. By way of example, the handle 15 may also contain a cooling apparatus or a light source for generating illumination light, which is guided to the illumination window 7 through optical waveguides.

The embodiments of a device according to the invention described in the following text and depicted in FIGS. 2a to 5 correspond to the exoscope 1 depicted in FIGS. 1a and 1b in terms of the external appearance.

Figure 2A:
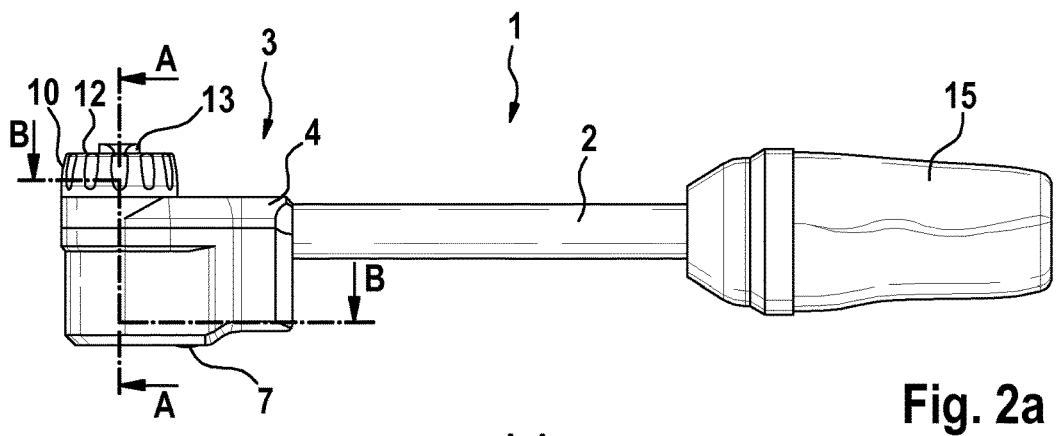
FIGS. 2a to 2c show a first exemplary embodiment of a device according to the invention in a side view and two sectional views.
Figure 2B:
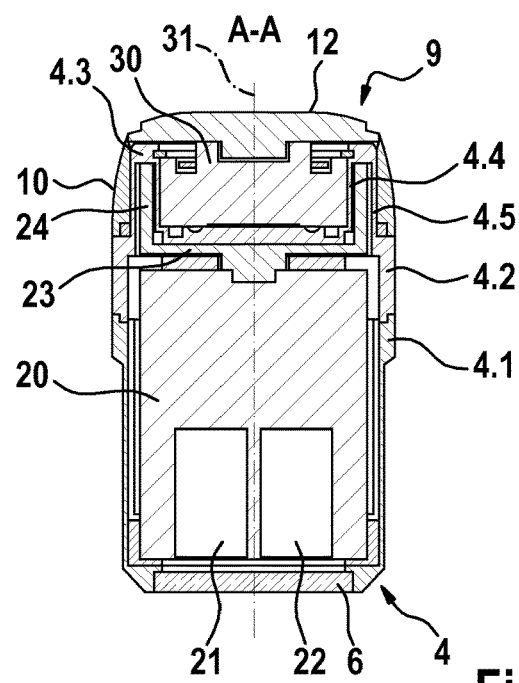
Figure 2C:
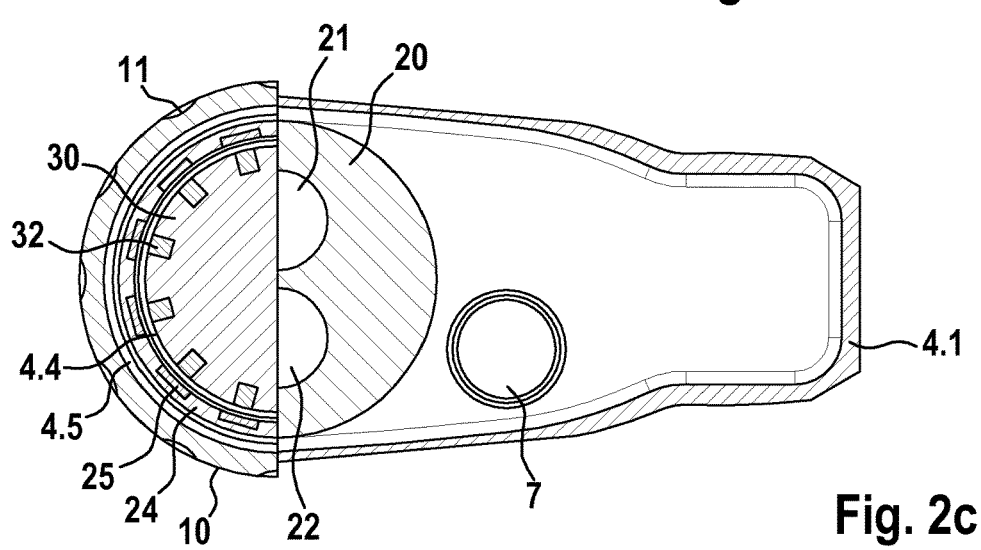
Figure 3:
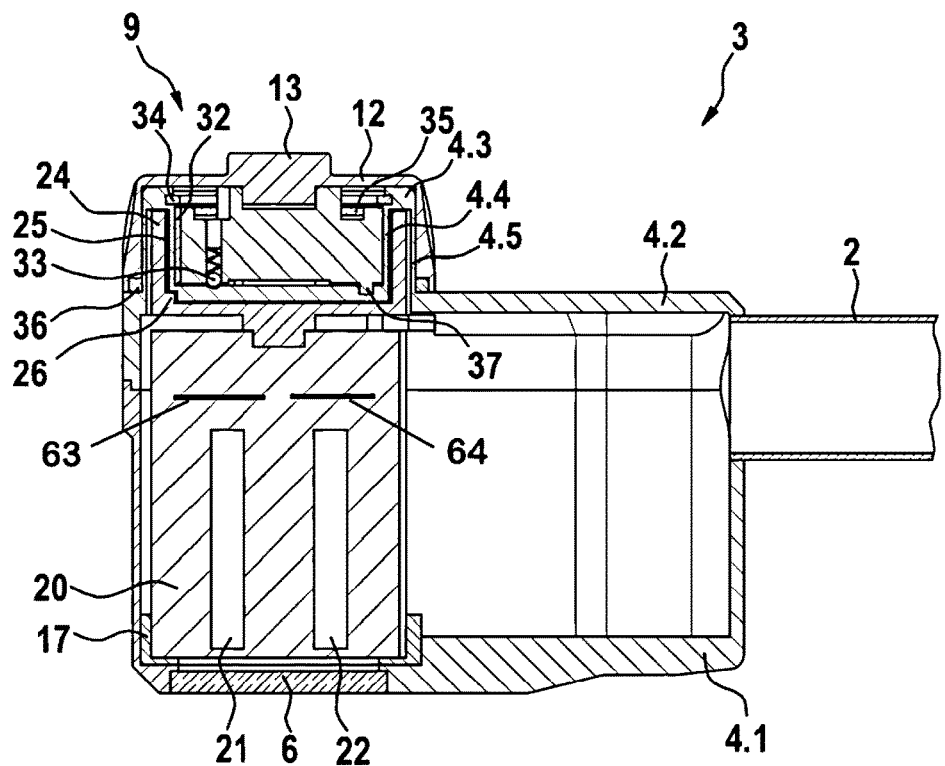
FIG. 3 shows a further sectional view of the first exemplary embodiment.

An exoscope in accordance with a first embodiment of the invention is depicted in FIGS. 2a to 2c and in FIG. 3. FIG. 2a shows a side view of such an exoscope 1, corresponding to that shown in FIGS. 1a and 1b; in this respect, reference is made to the description of FIGS. 1a and 1b. FIG. 2a shows two sectional lines, wherein the section A-A depicts a cross section in relation to the longitudinal axis of the shaft 2 and the section B-B depicts a horizontal longitudinal section in two different planes.

As shown in the cross-sectional illustration of FIG. 2b, the housing 4 is composed of a housing lower part 4.1 and a housing upper part 4.2, which are connected to one another in a hermetically sealed manner, for example by welding. The observation window 6 is inserted in a hermetically sealed manner into the base surface 5 formed by the housing lower part 4.1, for example by soldering, just like the illumination window 7 identifiable in FIG. 2c. Therefore, the housing 4 is hermetically sealed overall. Arranged within the interior of the housing 4 is an optical unit 20, which contains two objectives 21, 22, depicted in a symbolic manner, and further components (not depicted here), in particular two electronic image recorders assigned to the objectives 21, 22 and, optionally, pre-evaluation electronics. The direction of view of the optical unit or of the objectives is aligned at an angle of approximately 90° in relation to the longitudinal axis of the shaft 2.

A disk 23, which supports an erect hollow cylindrical second magnet support 24 on the outer circumference thereof, is connected to the optical unit 20 for rotation therewith. The disk 23 and the second magnet support 24 are likewise completely surrounded by the hermetically sealed housing 4, for which the latter has a hollow, erect ring region formed by an inner wall 4.4, an outer wall 4.5 and a cover region 4.3. As a result, the housing upper part 4.2 has a cup-shaped depression in the upper region thereof.

The rotary cap 9 is placed onto the housing upper part 4.2 in a rotatable manner, the circumferential region 10 of which rotary cap engages around the outside of the outer wall 4.5 of the housing upper part 4.2 surrounding the ring-shaped second magnet support 24. The circumferential region 10 of the rotary cap 9 or the rotary cap 9 overall is made from a suitable plastics material with low thermal conductivity in order to allow comfortable actuation of the rotary cap 9 for the user, even if the head part 3 has been heated by the thermal losses released therein. A cylindrical first magnet support 30 is connected to the rotary cap 9 for rotation therewith, which first magnet support is inserted with little play into the cup-shaped depression of the housing upper part 4.2. The rotary cap 9 with the cylinder 30 is mounted on the housing 4 in a rotatable manner. The optical unit 20 with the disk 23 and the second magnet support 24 is mounted within the housing 4 in a rotatable manner, wherein the optical unit 20 and the rotary cap 9 have a common axis of rotation 31. The axis of rotation 31 represents the central axis of the substantially cylindrically formed optical unit 20, of the disk 23, of the magnet supports 24, 30 and of the rotary cap 9. The objectives 21, 22 are arranged within the optical unit 20 in a symmetrical manner in relation to the axis of rotation 31.

As shown in a horizontal longitudinal section in FIG. 2c, a plurality of magnets 32 are inserted into the recesses in the lateral surface of the cylindrical magnet support 30, with said magnets being distributed uniformly along the circumference. The same number of magnets 25 have been inserted into the recesses of the inner cylindrical surface of the hollow cylindrical second magnet support 24. The magnets 25, 32 lying opposite one another are respectively aligned with opposite poles, such that, in the case of a first magnet 25, the magnetic north pole is directed upward and, in the case of a second magnet 32, arranged opposite thereto, the south pole is directed upward, or vice versa. Provision can also be made for a magnetic pole in the first magnet 25 to be directed inward, i.e. toward the second magnet 32, and for the opposite pole in the second magnet 32 to be directed outward, i.e. toward the first magnet 25. The pairs of mutually opposite first and second magnets 25, 32 arranged along the circumference may in each case have the same or alternating polarities. As a result of the magnetic attractive forces thus generated between the first and the second magnets 25, 32, the two magnet supports 24, 30 are coupled to one another magnetically such that the first magnet support 30 connected to the optical unit 20 follows a rotation of the second magnet support 24 connected to the rotary cap 9, optionally with an angle offset dependent on the friction of the mount of the optical unit 20 and the strength of the magnetic coupling.

Further details of the described first embodiment of the exoscope 1 are shown in the perpendicular longitudinal section depicted in FIG. 3. In the proximal region of the head part 3, the housing lower part 4.1 and the housing upper part 4.2 are terminated or connected to the shaft 2 in a hermetically sealed manner, which shaft may be hermetically sealed off in the proximal end region thereof (not depicted here). The optical unit 20 contains two objectives 21, 22, as only indicated symbolically in FIG. 3, and the electronic image recorders 63 and 64 assigned thereto. The ring-shaped second magnet support 24 connected to the optical unit 20 via the disk 23 for rotation therewith supports a plurality of second magnets 25 on the inner side thereof. The cylindrical first magnet support 30, which is connected to the rotary cap 9 for rotation therewith, supports a plurality of first magnets 32 on the outer side thereof. The magnets 25, 32 act as magnetic coupling elements, which interact through the relatively thin inner wall 4.4 of the housing 4. By way of example, to this end and as described above, the magnets 25 assigned to the optical unit may be arranged along the inner wall of the second magnet support 24 with the same or alternating polarity and the magnets 32 may be fastened to the outer wall of the magnet support 30 with the same number and with the same or a mirror-inverted arrangement. This produces magnetic coupling between the magnet supports 24, 30 and therefore between the rotary cap 9 and the optical unit 20 such that rotating the rotary cap 9 about the axis of rotation 31 (see FIG. 2b) is able to cause a rotation of the optical unit about the same axis of rotation.

A shape inhibitor in the form of a spring-mounted latching ball 33 can be arranged in the first magnet support 30, wherein the latching ball 33 engages in corresponding recesses of the housing upper part 4.2. Together with the first magnet support 30, the rotary cap 9 is secured on the ring-shaped cover region 4.3 of the housing upper part by means of a snap ring 34 and sealed with slide sealing rings 35, 36. Furthermore, provision is made for a stop 26 for restricting the angle of rotation of the optical unit 20 on the disk 23 and provision is made for stop 37 on the magnet support 30 for restricting the adjustment angle of the rotary cap 9. Both the stop 26 and the stop 37 interact with corresponding stops of the housing and, in addition to restricting the angles, also enable securing of ideal coupling between the magnetic coupling elements. In general, a range of ±90° is sufficient as an adjustment angle range. The optical unit 20 is mounted in the housing lower part 4.1 with a sliding bearing 17. A cable guide (not depicted here) for guiding supply and signal cables (likewise not depicted here) extending through the shaft 2 to the rotatable optical unit 20 is arranged in the interior of the housing 4.

Figure 4:
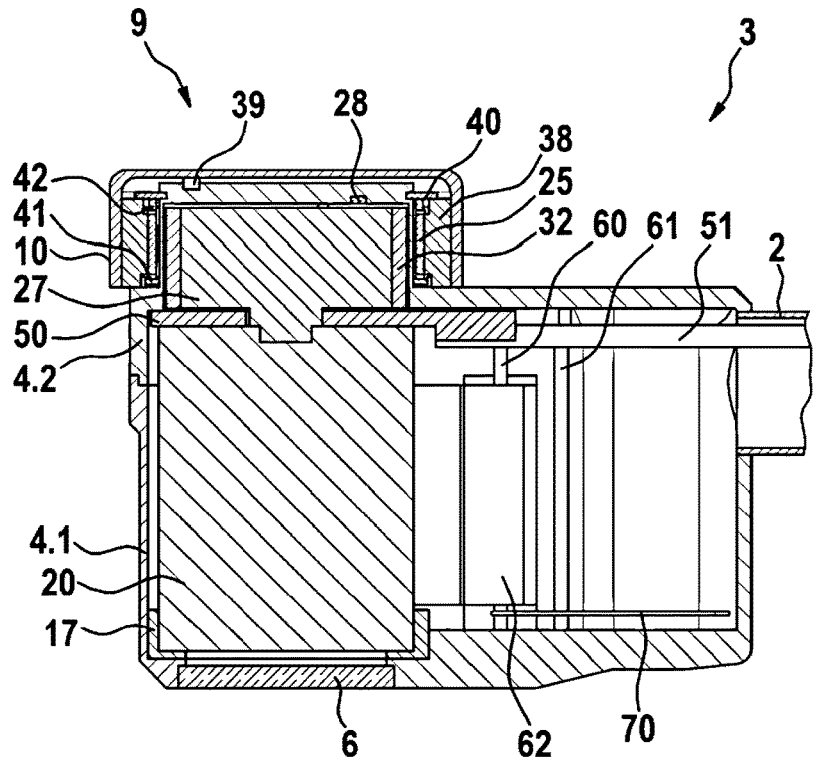
FIG. 4 shows a sectional view of a second exemplary embodiment of a device according to the invention.

FIG. 4 depicts the distal end region of a second embodiment of an exoscope according to the invention. Here, a cylindrical second magnet support 27 which supports second magnets 32 on the circumferential side is connected to the optical unit 20 for rotation therewith, said second magnets being magnetically coupled to first magnets 25 arranged on the inner side of the ring-shaped first magnet support 38, which is fastened to the circumferential region 10 of the rotary cap 9, through a wall of the housing upper part 4.2. The adjustment angle of the rotary cap 9 is restricted by a stop 39 while the angle of rotation of the optical unit 20 is restricted by a stop 28. Slide sealing rings 40, 41 are provided for sealing the rotary cap 9. Otherwise, the second exemplary embodiment of the invention may be embodied like the above-described first exemplary embodiment. The objectives 21, 22 and the electronic image recorders are not depicted in FIG. 4.

FIG. 4 depicts measures for guiding cables and for dissipating heat, which likewise can be employed in the exemplary embodiment described above. On the side opposite to the sliding bearing 17, the optical unit 20 is in contact with thermal conduction sheets 50 made of graphite, by means of which thermal losses generated in the optical unit 20 are conducted along to a heat pipe 51, as a result of which the thermal losses are dissipated through the shaft 2 into the proximal end region of the exoscope 1 or into the grip 15. In order to guide connection lines to the optical unit 20, provision is made for deflections 60, 81, via which a cable, which e.g. may be embodied as a flexible circuit board 62, is guided. A guide 70 for displacing the deflection 60 is indicated symbolically in FIG. 4.

Figure 5:
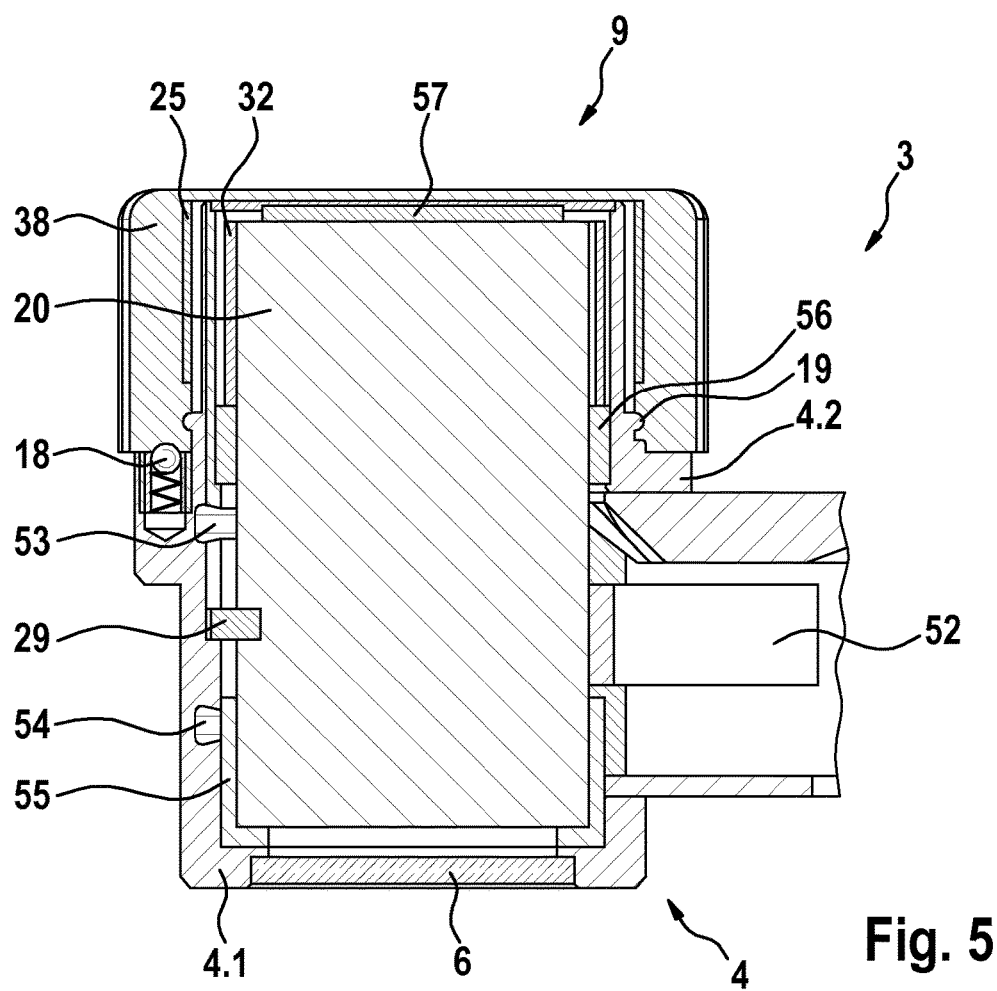
FIG. 5 shows a sectional view of a third exemplary embodiment of a device according to the invention.

FIG. 5, which shows a third embodiment of an exoscope according to the invention, depicts further measures for heat dissipation, which can be used additionally or alternatively to the measures described above in the exemplary embodiments described previously. As depicted schematically in FIG. 5, a graphite film embodied as a wiper 52 butting against the lateral surface of the optical unit 20 may serve for heat dissipation. Alternatively or additionally, heat pipes 53, 54 can be inserted into grooves of the housing 4 in an interlocking or cohesive manner in order to ensure effective cooling of the housing 4 and therefore of the optical unit 20. FIG. 5 shows a shape inhibitor comprising a sprung latching ball 18, which generates a latching effect and engages in the lower-side recesses of the first magnet support 38. Furthermore, in the embodiment shown in FIG. 5, provision is made for a stop 19 for restricting the adjustment angle of the rotary cap 9 and a stop 29 for restricting the angle of rotation of the optical unit 20. In this embodiment, the housing upper part 4.2 of the hermetically sealed housing is embodied as a number of parts, wherein the plurality of individual parts of the housing upper part 4.2, and also the housing upper part 4.2 and the housing lower part 4.1, are cohesively connected to one another, for example by welding. Here, the optical unit 20 is mounted in the housing via sliding bearings 55, 56 and 57. Otherwise, the embodiment shown in FIG. 5 corresponds to the one depicted in FIG. 4.

In order to observe an object field, for example an operation field in a surgical operation, the exoscope 1 is brought into a position at a distance of e.g. 25 to 70 cm above the operation field by means of a holding arm (not depicted in the figures) which engages on the shaft 2 with a gripper, wherein the shaft 2 is aligned substantially horizontally. Here, the exoscope 1 is oriented in such a way that it protrudes into the space above the operation field from a direction in such a way that the surgeon is impeded as little as possible; by way of example, the exoscope 1 can be directed in a manner facing the surgeon. Furthermore, the exoscope 1 is configured in such a way by rotation about the longitudinal axis of the shaft 2 that the direction of view of the stereo objective is directed downward so that the operation field can be illuminated by the illumination light emerging from the illumination window 7 and observed through the observation window 8 by means of the stereo optical system. The exoscope 1 is fixed in this position and orientation with the aid of the holder, in order to observe the operation field, the recorded stereoscopic image is depicted on a display apparatus suitable for the surgeon and optionally further persons and stored for documentation purposes. To the extent that erecting the displayed image and/or a setting of the stereo basis for an ideal spatial perception is already required here, this can be brought about by manual rotation of the rotary cap 9.

Within the scope of the surgical operation, it may be necessary to realign the exoscope. In particular, as a result of e.g. a positional change of the surgeon, it may be necessary to orientate the holding arm in such a way that the exoscope protrudes into the space above the operation field from a different direction; this corresponds to swiveling the exoscope about an axis parallel to the direction of view or about a central axis between the optical axes of the objectives 21, 22. In the process, there is a change in both the alignment of the displayed image and in the direction of the stereo basis, and so the orientation on the displayed image is made more difficult and the spatial impression may be lost. By manual rotation of the rotary cap 9, the surgeon or a different person can erect the image and restore the original direction of the stereo basis such that the spatial perception is unaffected.

For reasons of clarity, not all reference signs are depicted in all figures. Reference signs not explained in relation to one figure have the same meaning as in the remaining figures.

The invention claimed is:

1. A device for recording an image of an object field on a human or animal body from outside of the body, the device comprising:

a shaft;

an observation optical system arranged at a distal end of the shaft, the observation optical system configured to record the image of the object field, the observation optical system being a stereo optical system comprising at least one electronic image recorder configured to record a stereo image of the object field; and an optical unit, which comprises the observation optical system and is rotatable relative to the shaft and about a first axis of rotation approximately parallel to a direction of view of the observation optical system, the direction of view at approximately 90° in relation to a longitudinal axis of the shaft.

2. The device according to claim 1, wherein the optical unit comprises two objectives and two electronic image recorders; and wherein an electronic image recorder configured to record a half image of the stereo image of the object field is assigned to each objective.

3. The device according to claim 1, further comprising a hermetically sealed housing, within which the optical unit is held and mounted in a manner rotatable relative to the shaft and about the first axis of rotation.

4. The device according to claim 3, wherein, in order to permit rotation of the optical unit relative to the shaft and about the first axis of rotation, at least one first magnetic coupling element is arranged outside of the housing and configured to interact with at least one second magnetic coupling element which is connected to the optical unit and arranged within the housing.

5. The device according to claim 4, wherein the at least one first magnetic coupling element is connected to a manually actuatable operating element, which is rotatable about a second axis of rotation substantially parallel to the first axis of rotation.

6. The device according to claim 5, wherein the optical unit is arranged in a head part arranged at the distal end of the shaft.

7. The device according to claim 6, wherein the operating element is embodied as a rotary cap placed onto a side of the head part opposing the direction of view.

8. The device according to claim 5, wherein the at least one second magnetic coupling element is arranged on an outer side of a substantially cylindrical second magnet support connected to the optical unit and configured to rotate therewith and the at least one first magnetic coupling element is arranged on an inner side of a substantially ring-shaped first magnet support which is connected to the operating element and configured to rotate therewith and surrounds the second magnet support.

9. The device according to claim 5, wherein the at least one second magnetic coupling element is arranged on an inner side of a substantially ring-shaped second magnet support connected to the optical unit and configured to rotate therewith and the at least one first magnetic coupling element is arranged on an outer side of a substantially cylindrical first magnet support which engages with the substantially ring-shaped second magnet support and is connected to the operating element.

10. The device according to claim 5, further comprising a stop configured to act against the housing and restrict rotational movement of the operating element and the optical unit.

11. The device according to claim 5, wherein the operating element has one or more latching positions.

12. The device according to claim 1, wherein the optical unit is connected in a heat-conducting manner to a heat conductor arranged in the shaft, the heat conductor configured to dissipate thermal losses arising in the optical unit.

\* \* \* \* \*